(12) United States Patent
Ashley et al.

(10) Patent No.: US 8,109,968 B2
(45) Date of Patent: Feb. 7, 2012

(54) SUTURE LOCK

(75) Inventors: John E. Ashley, Oakland, CA (US);
David F. Lyons, Palo Alto, CA (US)

(73) Assignee: Anpa Medical, Inc., San Mateo, CA (US)

( * ) Notice: Subject to any disclaimer, the term of this patent is extended or adjusted under 35 U.S.C. 154(b) by 564 days.

(21) Appl. No.: 12/231,748

(22) Filed: Sep. 5, 2008

(65) Prior Publication Data

US 2009/0076546 A1    Mar. 19, 2009

Related U.S. Application Data

(63) Continuation-in-part of application No. 10/841,255, filed on May 7, 2004, now Pat. No. 7,862,584.

(60) Provisional application No. 60/967,531, filed on Sep. 5, 2007, provisional application No. 60/468,496, filed on May 7, 2003.

(51) Int. Cl.
*A61B 17/04* (2006.01)
*F16G 11/00* (2006.01)

(52) U.S. Cl. .......................................... 606/232; 24/130

(58) Field of Classification Search .................. 606/300, 606/232, 115 R, 129 R, 130; 289/13, 14; 24/115 R, 129 R, 130
See application file for complete search history.

(56) References Cited

U.S. PATENT DOCUMENTS

| | | | |
|---|---|---|---|
| 322,501 A * | 7/1885 | Taylor | 24/130 |
| 551,032 A | 12/1895 | Hemphill | |
| 3,498,575 A | 3/1970 | Downing | |
| 3,574,900 A | 4/1971 | Emery | |
| 3,988,810 A | 11/1976 | Emery | |
| 4,416,503 A | 11/1983 | Hayes | |
| 4,750,492 A | 6/1988 | Jacobs | |
| 4,787,660 A | 11/1988 | Mrazek | |
| 4,829,999 A * | 5/1989 | Auth | 24/115 R |
| 4,896,403 A | 1/1990 | Vouros | |
| 4,950,285 A | 8/1990 | Wilk | |
| 4,969,892 A | 11/1990 | Burton et al. | |

(Continued)

FOREIGN PATENT DOCUMENTS

GB    2365351 B    11/2002

(Continued)

OTHER PUBLICATIONS

USPTO Office Action dated Feb. 1, 2007 regarding U.S. Appl. No. 10/841,255, 19 pages.

(Continued)

*Primary Examiner* — Julian Woo
(74) *Attorney, Agent, or Firm* — Ryan Kromholz & Manion, S.C.

(57) ABSTRACT

A suture lock according to the present invention sufficiently secures a suture thread in place in a quick and efficient manner. It eliminates the need for a laparoscopic surgeon to tie complex or multi-step knots. The suture lock generally comprises a suture lock body having a suture channel that allows a suture thread to be drawn into the suture lock body. A plurality of teeth extends into an opening of the suture channel in such a manner that an inserted suture thread will be locked in place. In addition, a guide portion eases insertion of a suture thread free end by simplifying relative rotational adjustment of the lock. An embodiment of the suture lock may be fabricated from a material or materials that naturally dissolve within the human body.

21 Claims, 11 Drawing Sheets

U.S. PATENT DOCUMENTS

| | | | |
|---|---|---|---|
| 5,037,433 A | 8/1991 | Wilk et al. |
| 5,068,495 A | 11/1991 | Dahl-Bettermann-Winand |
| 5,078,731 A | 1/1992 | Hayhurst |
| 5,123,913 A | 6/1992 | Wilk et al. |
| 5,160,339 A | 11/1992 | Chen et al. |
| 5,171,251 A | 12/1992 | Bregen et al. |
| 5,234,449 A | 8/1993 | Bruker et al. |
| 5,282,832 A | 2/1994 | Toso et al. |
| 5,330,442 A | 7/1994 | Green et al. |
| 5,372,604 A | 12/1994 | Trott |
| 5,376,101 A | 12/1994 | Green et al. |
| 5,383,905 A | 1/1995 | Golds et al. |
| 5,391,173 A | 2/1995 | Wilk |
| 5,409,499 A | 4/1995 | Yi |
| 5,411,522 A | 5/1995 | Trott |
| 5,413,585 A | 5/1995 | Pagedas |
| 5,441,224 A | 8/1995 | Ludwig |
| 5,472,452 A | 12/1995 | Trott |
| 5,474,572 A | 12/1995 | Hayhurst |
| 5,500,001 A | 3/1996 | Trott |
| 5,501,683 A | 3/1996 | Trott |
| 5,501,696 A | 3/1996 | Trott |
| 5,514,159 A | 5/1996 | Matula et al. |
| 5,520,703 A | 5/1996 | Essig et al. |
| 5,522,120 A | 6/1996 | Brinning |
| 5,626,590 A | 5/1997 | Wilk |
| 5,630,824 A | 5/1997 | Hart |
| 5,649,940 A | 7/1997 | Hart et al. |
| 5,665,109 A | 9/1997 | Yoon |
| 5,669,935 A | 9/1997 | Rosenman et al. |
| 5,681,351 A | 10/1997 | Jamiolkowski et al. |
| 5,683,418 A | 11/1997 | Luscombe et al. |
| 5,725,556 A | 3/1998 | Moser et al. |
| 5,735,877 A | 4/1998 | Pagedas |
| 5,741,301 A | 4/1998 | Pagedas |
| 5,782,864 A | 7/1998 | Lizardi |
| 5,806,452 A | 9/1998 | Benoit |
| 5,810,853 A | 9/1998 | Yoon |
| 5,814,052 A | 9/1998 | Nakao et al. |
| 5,879,371 A | 3/1999 | Gardiner et al. |
| 5,895,393 A | 4/1999 | Pagedas |
| 5,906,620 A | 5/1999 | Nakao et al. |
| 5,961,538 A | 10/1999 | Pedlick et al. |
| 5,980,524 A | 11/1999 | Justin et al. |
| 6,010,525 A | 1/2000 | Bonutti et al. |
| 6,015,428 A | 1/2000 | Pagedas |
| 6,066,160 A | 5/2000 | Colvin et al. |
| 6,074,395 A | 6/2000 | Trott et al. |
| 6,080,184 A | 6/2000 | Peters et al. |
| 6,096,060 A | 8/2000 | Fitts et al. |
| 6,143,017 A | 11/2000 | Thal |
| 6,149,669 A | 11/2000 | Li |
| 6,159,234 A | 12/2000 | Bonutti et al. |
| 6,163,936 A | 12/2000 | Benoit |
| 6,231,592 B1 | 5/2001 | Bonutti et al. |
| 6,260,498 B1 * | 7/2001 | Cochran .................. 24/130 |
| 6,296,659 B1 | 10/2001 | Foerster |
| 6,319,271 B1 | 11/2001 | Schwartz et al. |
| 6,432,123 B2 | 8/2002 | Schwartz et al. |
| 6,464,713 B2 | 10/2002 | Bonutti |
| 6,475,229 B1 | 11/2002 | Pagedas |
| 6,475,230 B1 | 11/2002 | Bonutti et al. |
| 6,527,794 B1 | 3/2003 | McDevitt et al. |
| 6,527,795 B1 | 3/2003 | Lizardi |
| 6,533,795 B1 | 3/2003 | Tran et al. |
| 6,551,330 B1 | 4/2003 | Bain et al. |
| 6,592,609 B1 | 7/2003 | Bonutti |
| 6,605,096 B1 | 8/2003 | Ritchart |
| 6,641,597 B2 | 11/2003 | Burkhart et al. |
| 6,660,023 B2 | 12/2003 | McDevitt et al. |
| 2004/0044366 A1 | 3/2004 | Bonutti et al. |
| 2004/0260344 A1 | 12/2004 | Lyons et al. |
| 2005/0177181 A1 | 8/2005 | Kagan et al. |

FOREIGN PATENT DOCUMENTS

| | | |
|---|---|---|
| GB | 2337934 B | 2/2003 |
| GB | 2379885 B | 5/2003 |

OTHER PUBLICATIONS

USPTO Office Action dated Jul. 18, 2007 regarding U.S. Appl. No. 10/841,255, 8 pages.

USPTO Office Action dated Nov. 14, 2007 regarding U.S. Appl. No. 10/841,255, 7 pages.

USPTO Interview Summary dated Jan. 15, 2008 regarding U.S. Appl. No. 10/841,255, 2 pages.

USPTO Office Action dated Mar. 18, 2008 regarding U.S. Appl. No. 10/841,255, 8 pages.

USPTO Office Action dated Aug. 15, 2008 regarding U.S. Appl. No. 10/841,255, 8 pages.

USPTO Office Action dated Sep. 22, 2009 regarding U.S. Appl. No. 10/841,255, 12 pages.

USPTO Interview Summary dated Nov. 7, 2008 regarding U.S. Appl. No. 10/841,255, 2 pages.

USPTO Office Action dated Feb. 12, 2009 regarding U.S. Appl. No. 10/841,255, 10 pages.

USPTO Office Action dated Jun. 7, 2010 regarding U.S. Appl. No. 10/841,255, 7 pages.

USPTO PCT Notification of Transmittal of International Preliminary Report on Patentability, regarding PCT/US08/10404, dated May 24, 2010, 8 pages.

* cited by examiner

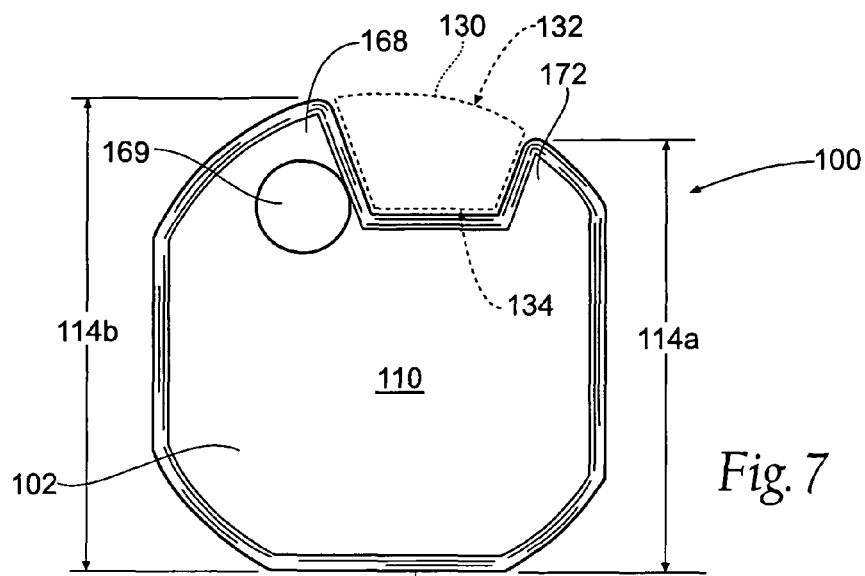
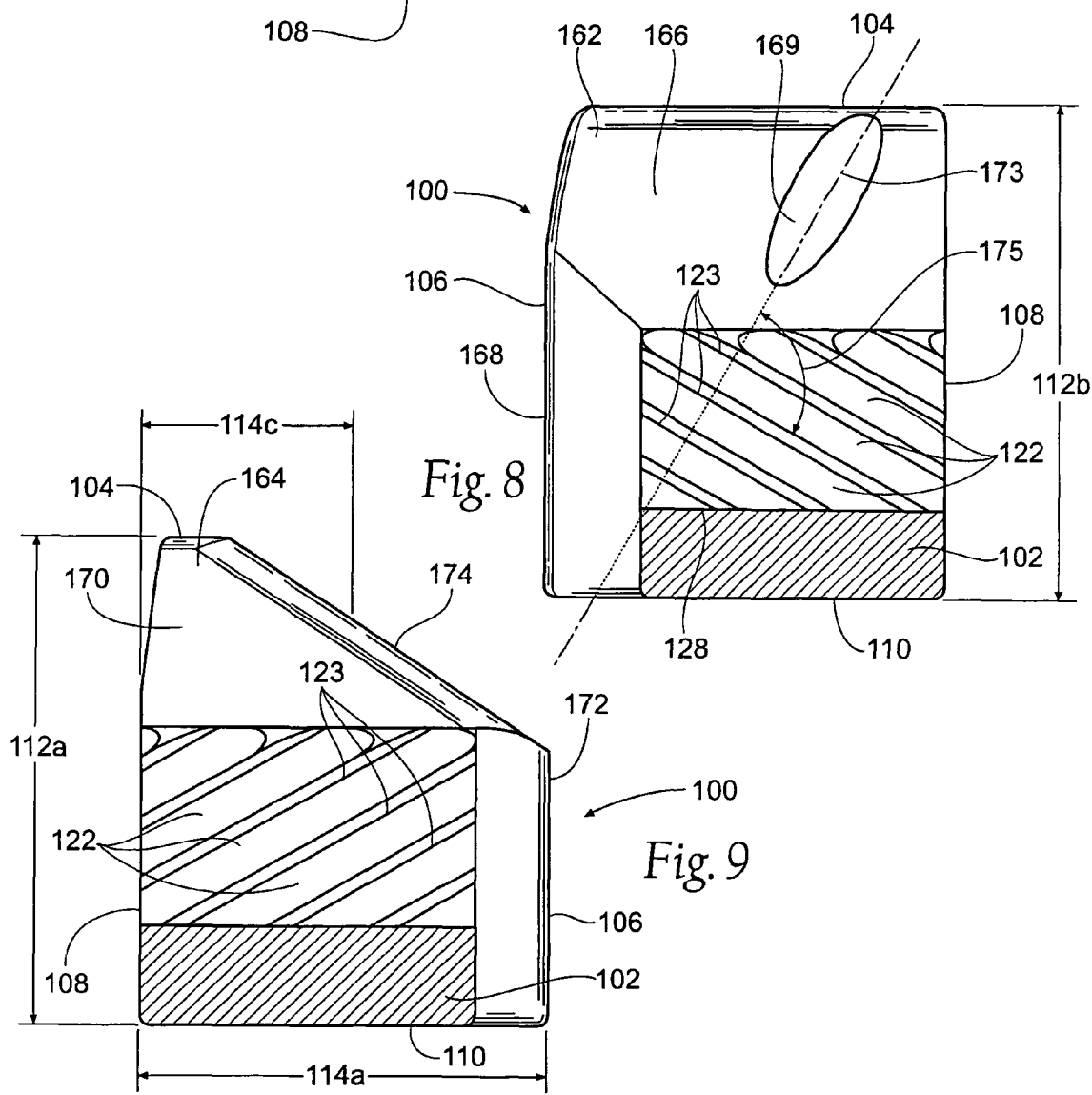
Fig. 7
Fig. 8
Fig. 9

SUTURE LOCK

RELATED APPLICATIONS

This application claims the benefit of U.S. Provisional Patent Application Ser. No. 60/967,531, entitled SUTURE LOCK, filed on Sep. 5, 2007. This application is a continuation-in-part of U.S. patent application Ser. No. 10/841,255, entitled SUTURE LOCK, filed on May 7, 2004, now U.S. Pat. No. 7,862,584, which claims the benefit of U.S. Provisional Patent Application Ser. No. 60/468,496, filed on May 7, 2003.

BACKGROUND OF THE INVENTION

The need for this invention arises from surgical practice and procedures, particularly surgical practice and procedures using laparoscopic instruments. Utilizing laparoscopic instruments involves making small incisions in the area of the surgical site. An endoscope may be inserted into one of the incisions to view the field of the operation inside the patient and laparoscopic surgical instruments are inserted into the same or other incisions and manipulated from outside the patient's body using video screen visualization, usually enlarged, to guide the work.

Anything that can reduce the number of steps to be performed during surgery can markedly reduce the stress of the procedure, both on the patient and on the doctor. Reducing the number of steps also reduces the time involved for the procedure, which is a priority in invasive procedures. Surgeons performing such operations are under considerable stress because remote manipulation of the surgical instruments using a video screen for visualization, rather than seeing the site of the operation directly, requires the learning of a great many techniques that are radically different from those performed when the surgical site is open to view. The required techniques include indirect hand-eye coordination and the cooperation between surgeons to place and secure sutures at the surgical site.

The placing of sutures during a laparoscopic surgical procedure may require two surgeons. The surgeons must cooperate in a multi-step process performed with multiple surgical instruments to manipulate the suture needle and the suture thread. The needle and suture thread are passed back and forth from one to the other, while placing the sutures by tying one or more knots.

Finally, prior sutures have generally been tightened and secured by tying knots in the suture thread. Such knots permanently fix a suture in place and are not able to be removed once in place without removing the entire suture. While some knots have been designed to be tightened further after placement, none allow the surgeon to loosen them if needed to reduce excessive tension on the tissue, which can prevent blood flow to the wound inhibiting healing, causing sclerosis and producing excessive scare tissue.

Suture locks and cooperating devices have been developed to simplify the laparoscopic surgical process. For instance, suture locks disclosed in U.S. Pat. Nos. 5,413,585, 5,735,877, 5,741,301, 5,895,393, 6,015,428 and 6,475,229, the specifications of which are incorporated herein by reference, have made the surgical process easier.

Wilk, U.S. Pat. No. 5,391,173, describes a suture device for locking a suture. The device requires that a suture is forced into a small opening or inserted into a larger opening that does not have a retaining mechanism. Colvin et al., U.S. Pat. No. 6,066,160, describes a suture locking device that requires threading of the suture through a small aperture. Schwartz et al., U.S. Pat. No. 6,432,123, describes a suture locking device that uses a locking ring to hold the suture in place. These patents contain advancements over the prior art, but still leave room for improvement, such as the ease of securing a suture thread, the overall time needed to properly complete a suture, or the ability to adjust a suture to increase or decrease suture tension as needed.

SUMMARY OF THE INVENTION

A suture lock according to the present invention sufficiently secures a suture thread in place in a quick and efficient manner. This novel design allows a single surgeon, perhaps working in a laparoscopic environment, to suture a surgical site with one or more suture locks and without the need of tying complex or multi-step knots. The suture lock generally comprises a body having a suture channel that allows a suture thread to be drawn into the body. A plurality of teeth extends into an opening of the suture channel in such a manner that an inserted suture thread will be locked in place. In addition, an embodiment of the present invention allows a suture thread, which was previously drawn into and secured by the suture lock body, to be released by a surgeon if desired, for example to reduce suture tension, and to be reengaged in its secured, cinched state. Furthermore, an embodiment of the present invention may be fabricated from a material or materials that naturally dissolve within the human body.

According to any embodiment of a suture lock according to the present invention, such suture lock includes a suture lock body, which may be a unitary member, having a front surface generally opposed from a back surface, and a left surface extending at least partially between and coupled to the front surface and the back surface. A right surface of the body is generally opposed from the left surface, the right surface and the left surface defining a width therebetween. The suture lock body also has a bottom surface extending between and coupled to the front surface and the back surface, the bottom surface also extending between and coupled to the right surface and the left surface. A top surface is generally opposed from the bottom surface, the top surface and the bottom surface defining a height therebetween. The suture lock body also includes a first channel formed in the right surface, the first channel extending longitudinally through the top surface and through the bottom surface. The first channel extends laterally between the front surface and the back surface. The first channel extends between a first open end at the right surface and a first terminal end, the first channel defining generally opposed front and back right guide wings. The first open end may be laterally wider than the first terminal end, thereby providing a funneling effect. Disposed at least partially in the first channel is a suture locking mechanism. A suture attachment site is also provided as a part of the lock body, preferably separate from the suture locking mechanism.

According to any embodiment of a suture lock according to the present invention, the suture locking mechanism may include a plurality of teeth, at least two of which have converging longitudinal edges. The plurality of teeth may include one or more pairs of symmetrical teeth. The converging longitudinal edges may S be at least substantially coplanar. At least two of the teeth may be located closer to the first terminal end than to the first open end. At least two pairs of the teeth may be located closer to the first terminal end than to the first open end.

According to any embodiment of a suture lock according to the present invention, the suture locking mechanism may include a predetermined grit of abrasive bonded to at least a portion of the first channel.

According to any embodiment of a suture lock according to the present invention, the suture attachment site may include a through bore. The through bore may extend through the left surface and through the back right guide wing. The through bore may be formed along a longitudinal bore axis, the longitudinal bore axis disposed at a through bore angle relative to the bottom surface. The longitudinal bore axis may be oriented substantially perpendicular skew to the converging longitudinal edges of at least two teeth, if utilized for the locking mechanism. The through bore angle may be an angle of between about zero degrees and about forty-five degrees. For example, the through bore angle may be an angle of about twenty-five degrees. Affixed to the suture lock body, such as by an adhesive, may be a suture thread extending at least partially through the through bore.

According to any embodiment of a suture lock according to the present invention, the front right guide wing and the back right guide wing may be asymmetric. Such asymmetry may be provided, for example, by the front right guide wing having a sloped top surface.

According to any embodiment of a suture lock according to the present invention, the suture lock may further include a second channel formed in the top surface, the second channel extending longitudinally through the left surface and through the terminal end of the first channel. The second channel may extend laterally between the front surface and the back surface. The second channel may extend between a second open end at the top surface and a second terminal end, and the second channel may form generally opposed front and back top guide wings. The first open end may be laterally wider than the first terminal end and the second open end may be laterally wider than the second terminal end. The height measured through the front top guide wing may be less than the height measured through the back top guide wing.

BRIEF DESCRIPTION OF THE DRAWINGS

FIG. 7 is a left elevation view of the embodiment of FIG. 1.

FIG. 8 is a cross-sectional view taken along line 8-8 of FIG. 5.

FIG. 9 is a cross-sectional view taken along line 9-9 of FIG. 4.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structures. While the preferred embodiment has been described, the details may be changed without departing from the invention, which is defined by the claims. While terms such as top, bottom, front, rear, left and right are used in describing the invention, such terms are not intended to be limiting, but are used merely to aid in an understanding of the invention.

Figure 1:
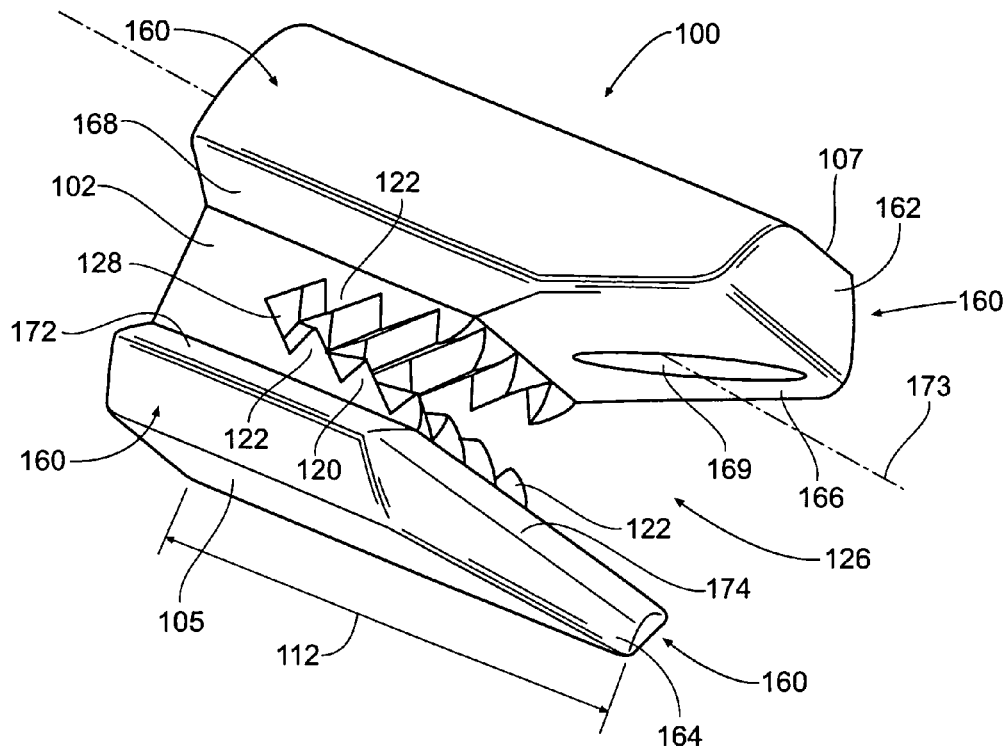
FIG. 1 is a top-right perspective view of a first embodiment of a suture lock according to the present invention.

FIG. 1 depicts a first perspective view of an embodiment 100 of a suture lock according to the present invention. Referring also to FIGS. 2-9, the suture lock 100 is preferably a unitary molded suture lock body 102 having a locking mechanism 120 and a guiding portion 160. The suture lock body 102 preferably has a front surface 105 generally opposed from a back surface 107. The body 102 further includes a left surface 110 extending at least partially between and coupled to the front surface 105 and the back surface 107. A right surface 104 generally opposes the left surface 110. The right surface 104 and the left surface 110 generally define a width 112 therebetween. A bottom surface 108 of the body 102 extends between and is coupled to the front surface 105 and the back surface 107. The bottom surface 108 also extends between and is coupled to the right surface 104 and the left surface 110. The body 102 further includes a top surface 106 generally opposed from the bottom surface 108, where the top surface 106 and the bottom surface 108 define a height 114 therebetween. The locking mechanism 120 preferably includes a plurality of teeth 122 disposed at least partially in a first channel 124 formed in the right surface 104 of the suture lock body 102. Alternately, the locking mechanism 120 may be any number of variations of high friction surfaces or geometries. For example surfaces composed of multiple barbs or hooks disposed at least partially in the first channel 124, surfaces of varying grits of bonded abrasive provided in the first channel 124, rasp-like surfaces composed of patterned ridges disposed at least partially in the first channel 124, or any variety of high friction surfaces well know by those skilled in the art can be used as the locking mechanism 120. The first channel 124 preferably extends longitudinally through the top surface 106 and through the bottom surface 108 and laterally between the front surface 105 and the back surface 107. A pair or plurality of pairs of opposing teeth 122 may be disposed along opposite sides of the first channel 124, having converging longitudinal edges 123 tapering generally towards each other from a first open end 126 of the first channel 124 towards a first terminal end 128 of the first channel 124. The teeth 122 included in a pair of opposing teeth are preferably symmetrical. The converging longitudinal edges 123 of opposing paired teeth 122 are preferably at least substantially coplanar and the converging longitudinal edges 123 of adjacent teeth 122, if more than one tooth 122 is provided along a side of the first channel 124, are preferably at least substantially coplanar and at least substantially parallel. The first open end 126 is preferably wider than a desired suture thread, thereby easing the process of feeding the thread into the suture lock 100. On the contrary, the generally V-shaped taper towards the first terminal end 128 is preferably smaller than the desired suture thread, thereby providing a wedging effect to secure the thread to the lock 100. Therefore, the first open end 126 is preferably laterally wider than the first terminal end 128. The first channel 124 preferably defines a back right guide wing 162 generally opposed from a front right guide wing 164, as further discussed below.

The body 102 also preferably includes a second channel 130 formed in the top surface 106. The second channel 130 preferably extends longitudinally through the left surface 110 and through the terminal end 128 of the first channel 124, and laterally between the front surface 105 and the back surface 107. The second channel 130 is provided with an open end 132 at the top surface 106 and a terminal end 134 generally opposed from the open end 132. The second channel 130 preferably defines a back top guide wing 168 generally opposed from a front top guide wing 172, as further discussed below.

Figure 2:
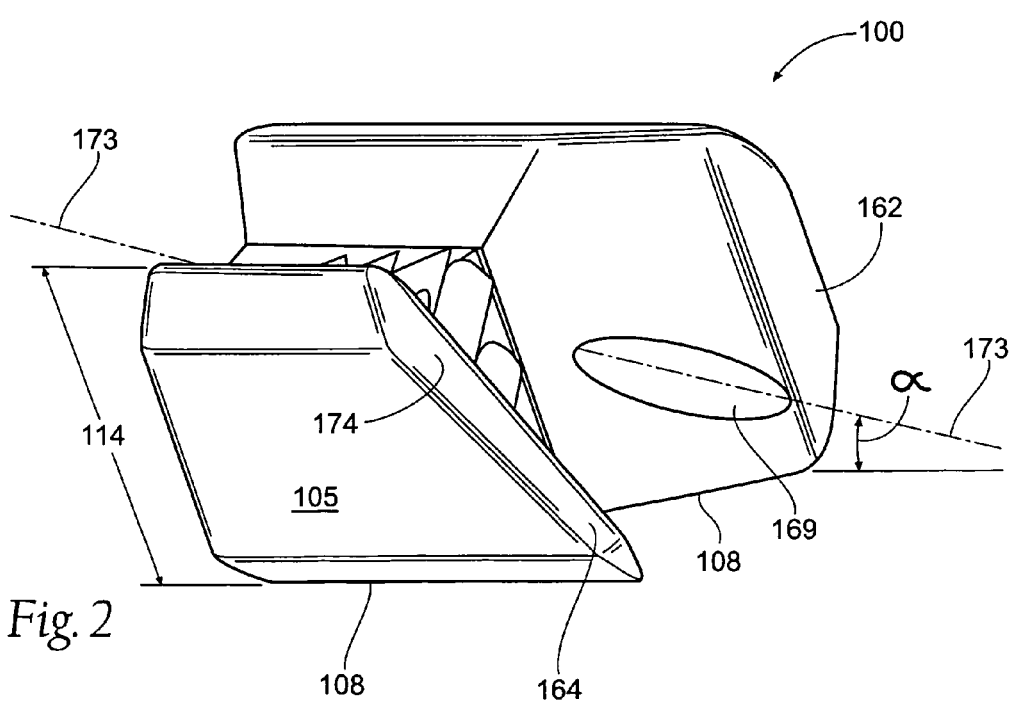
FIG. 2 is a front-right perspective view of the embodiment of FIG. 1.

Still referring to FIGS. 1-9, a guiding portion 160 is provided to assist in directing a suture thread towards the locking mechanism 120, or conversely, orienting the lock 100 so that proper engagement of a thread is possible. The guiding portion 160 includes the back right guide wing 162 and front right guide wing 164 both defined by the first channel 124, and the back top guide wing 168 and back front guide wing 172, which are defined by the second channel 130. The back right guide wing 162 extends preferably angularly away from the locking mechanism 120 along a first sloped side 166 of the first channel 124. A suture attachment site 169 preferably extends through the lock 100 from the left surface 110 at least partially through the back right guide wing 162. The suture attachment site 169 may be a through bore or lumen 171, as shown, formed during the molding of a lock 100. Alternatively, the suture attachment site 169 may include the over molding of a suture thread by the material from which the suture lock 100 is made. The through bore 171 is preferably formed along a longitudinal bore axis 173 disposed at a through bore angle α relative to the bottom surface 108 of the lock 100, as shown in FIG. 2. While the through bore angle α may vary, such as between zero and 90 degrees, depending upon the particular use of the device, a preferred through bore angle α is about 25 degrees. Alternatively, or additionally, the longitudinal bore axis 173 is provided skewed to the converging longitudinal edges 123 of at least two of the teeth 122, at a preferred angle 175, such as substantially orthogonally skew as shown. Furthermore, although preferably separated from the teeth 122, the suture attachment site 169 is not restricted to the position shown. In other words, the site 169 may be altered depending upon physician preference or treatment requirements, such as placing the suture attachment site 169 through the front right guide wing 164, the back top guide wing 168, the front top guide wing 172, or even in a medial location through the device.

The front right guide wing 164 also extends preferably angularly away from the locking mechanism 120, and is preferably asymmetric to the back right guide wing 162. The top surface 106 along at least a portion of the front right guide wing 164 is preferably provided as an insertion chamfer 174 such that a height 114c measured through the front right guide wing 164 is less than a height 114a measured through the front top guide wing 172. Such a design allows free passage of a suture thread past the front right guide wing 164 to make physical contact with the back right guide wing 162. The combination of the right guide wings 162,164 and the top guide wings 168,172 provide assisted directionality or tapering towards the locking mechanism 120, preferably from three directions. While the front surface 105, the back surface 107, the bottom surface 108 and the left surface 110 of the lock 100 are shown as being substantially planar with some rounded corners, the outer shape could also be curved, cylindrical or spherical. Additionally, while the front surface 105, the bottom surface 108 and left surface 110 are shown as being pairwise at least substantially orthogonal, and the back surface 107, the bottom surface 108 and left surface 110 are shown as being pairwise at least substantially orthogonal, other configurations are contemplated.

Figure 3:
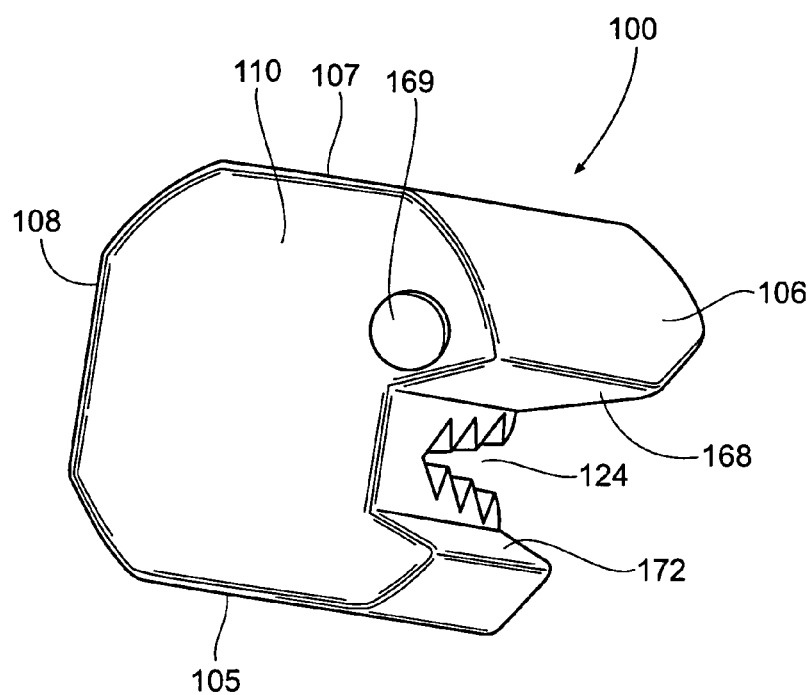
FIG. 3 is a top-left perspective view of the embodiment of FIG. 1.
Figure 4:
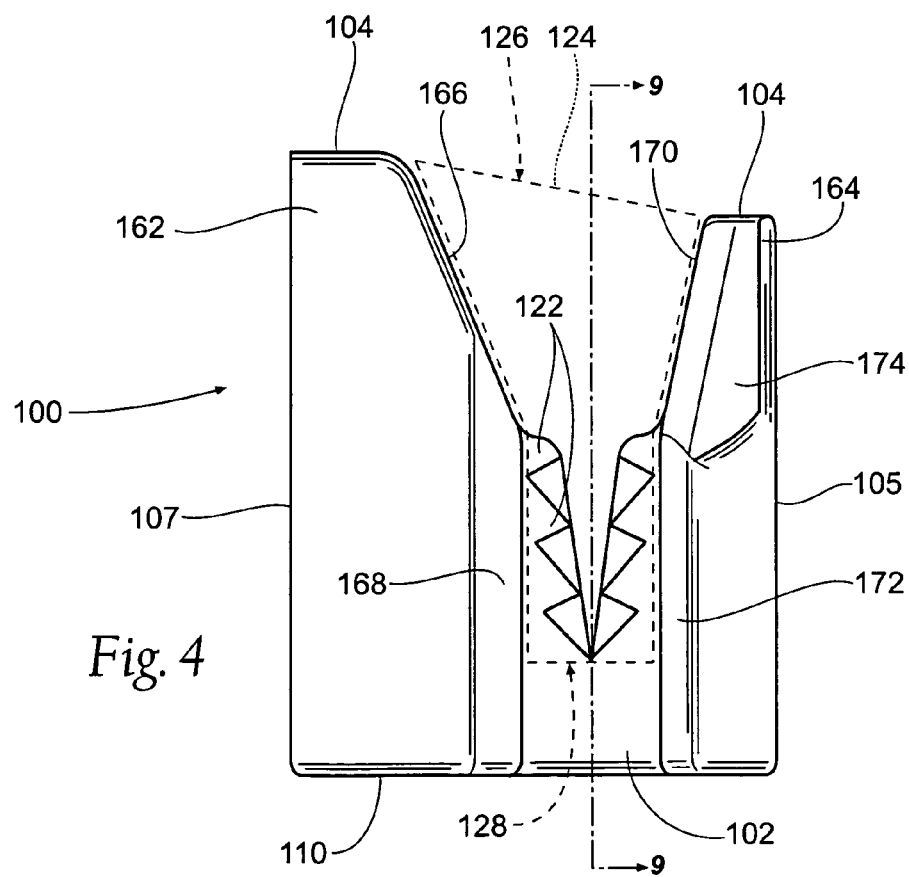
FIG. 4 is a top plan view of the embodiment of FIG. 1.
Figure 5:
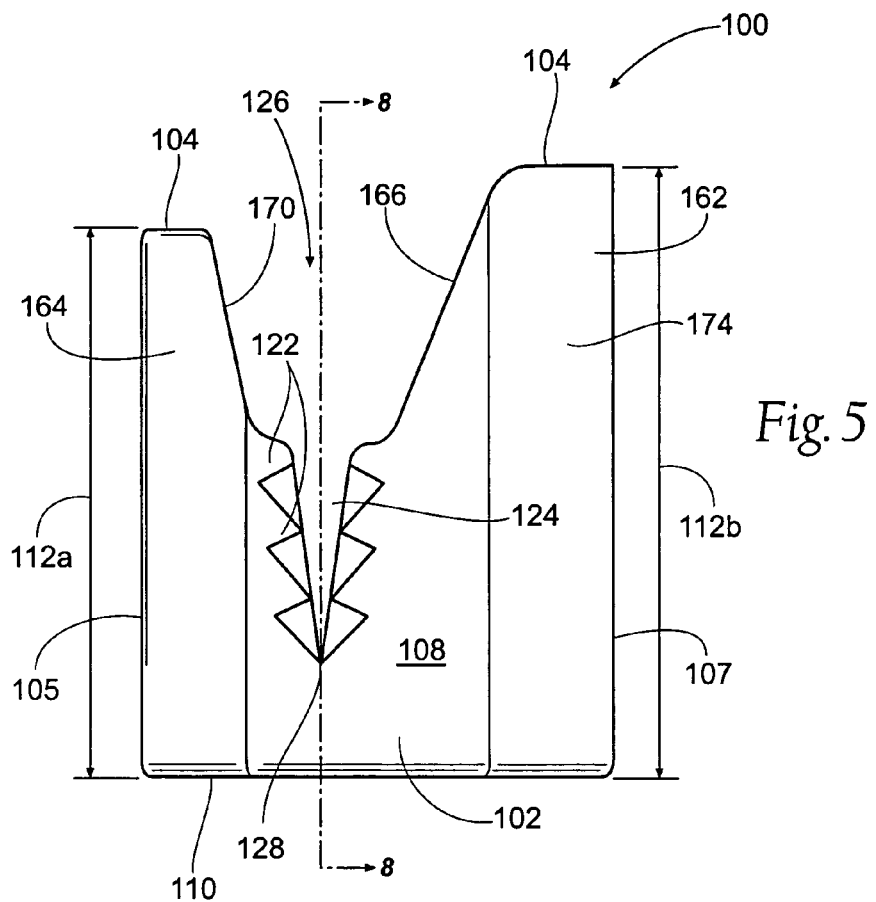
FIG. 5 is a bottom plan view of the embodiment of FIG. 1.
Figure 6:
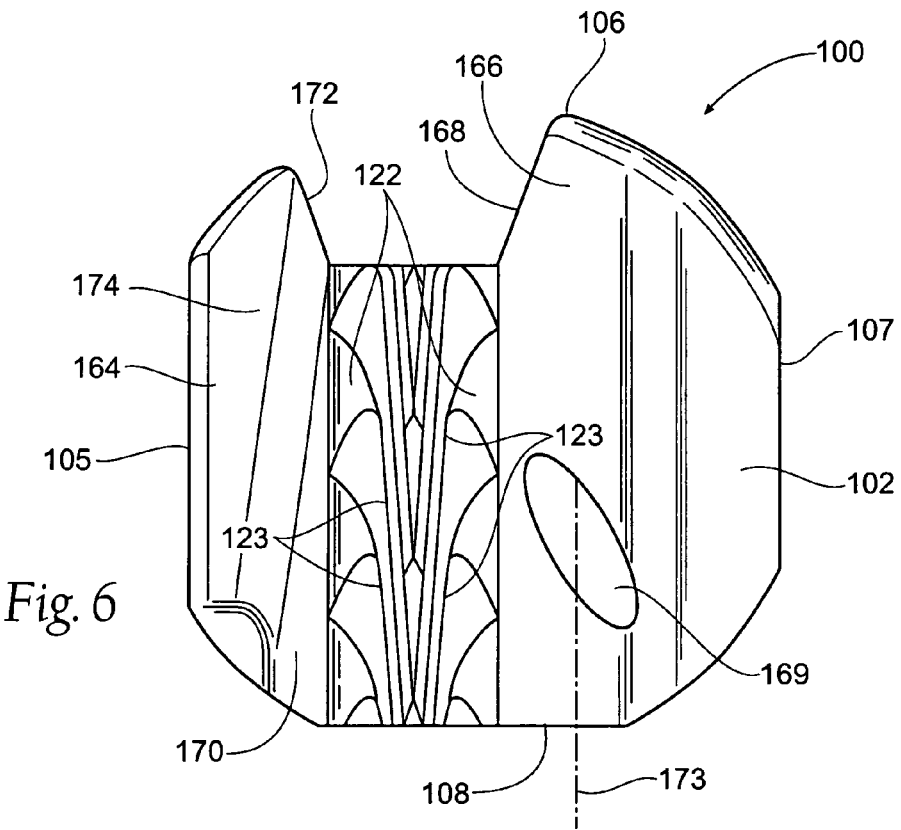
FIG. 6 is a right elevation view of the embodiment of FIG. 1.

FIG. 3 provides a perspective view of the left surface 110 of the lock 100 from FIG. 1, in which the suture thread attachment site 169 may be seen clearly as extending through the suture lock body 102. FIGS. 4-7 provide elevation and plan views of the embodiment of FIG. 1. As shown in FIG. 5, the width 112 of the body 102 may vary. For instance, a width 112a measured through the front right guide wing 164 may be less than a width 112b measured through the back right guide wing 162. Additionally, as shown in FIG. 7, the height 114 of the body 102 may vary. For instance, a height 114a measured through the front top guide wing 172 may be less than a height 114b measured through the back top guide wing 168. FIG. 8 and FIG. 9 provide opposing cross-sectional views from proximate the middle of the first channel 124.

Figure 10:
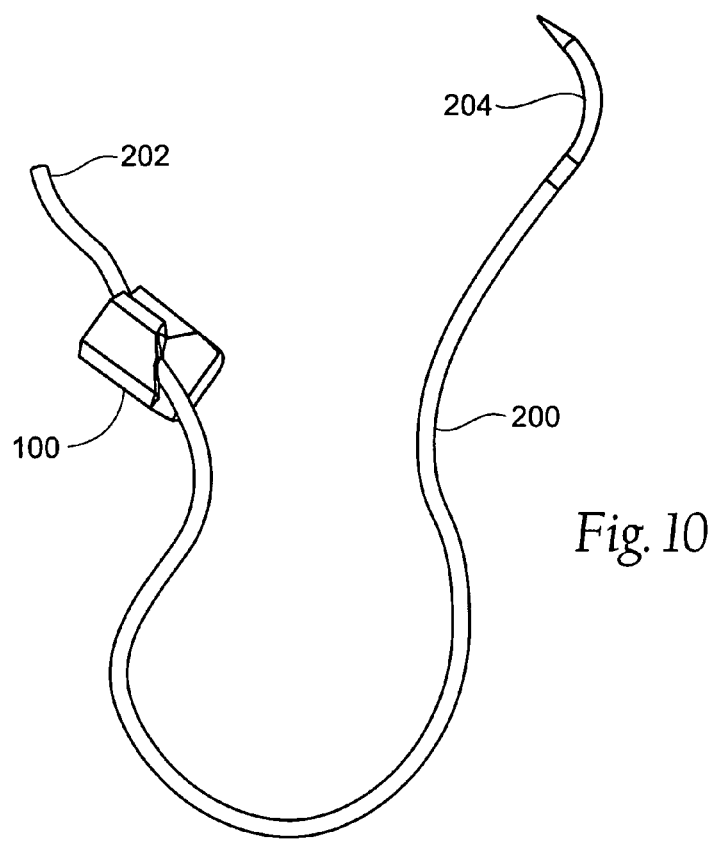
FIG. 10 is a third perspective view of the embodiment of FIG. 1, further including a suture thread inserted through a suture thread aperture.

FIGS. 10-15, inclusive, generally demonstrate a use of a device 100 according to the present invention. In FIG. 10, a suture thread 200 has been fastened to a suture lock 100 according to the present invention. If the lock 100 was provided with a suture attachment lumen, such as that illustrated in FIGS. 1-9, the suture thread 200 may be fastened in the lumen by any desirable method. For example, the thread may be held in place by an adhesive or knots may be formed in the thread 200 on either side of the lock 100. Instead of being provided with a suture attachment lumen, the thread 200 may have been overmolded during the formation of the lock 100. In other words, the lock 100 may have been formed around the thread 200, thereby binding the thread 200 in the material of the lock 100. Regardless of the method of attachment of the thread 200 to the suture lock 100, it may be preferable to leave a working end 202 extending from the lock 100. Towards or at the end of the suture thread 200 opposite the suture lock 100, a suture needle 204 is provided. The suture needle 204 may be crimped or adhered to the end of the suture thread 200, or the suture thread 200 may be threaded through an eye provided in the needle (not shown).

Figure 11:
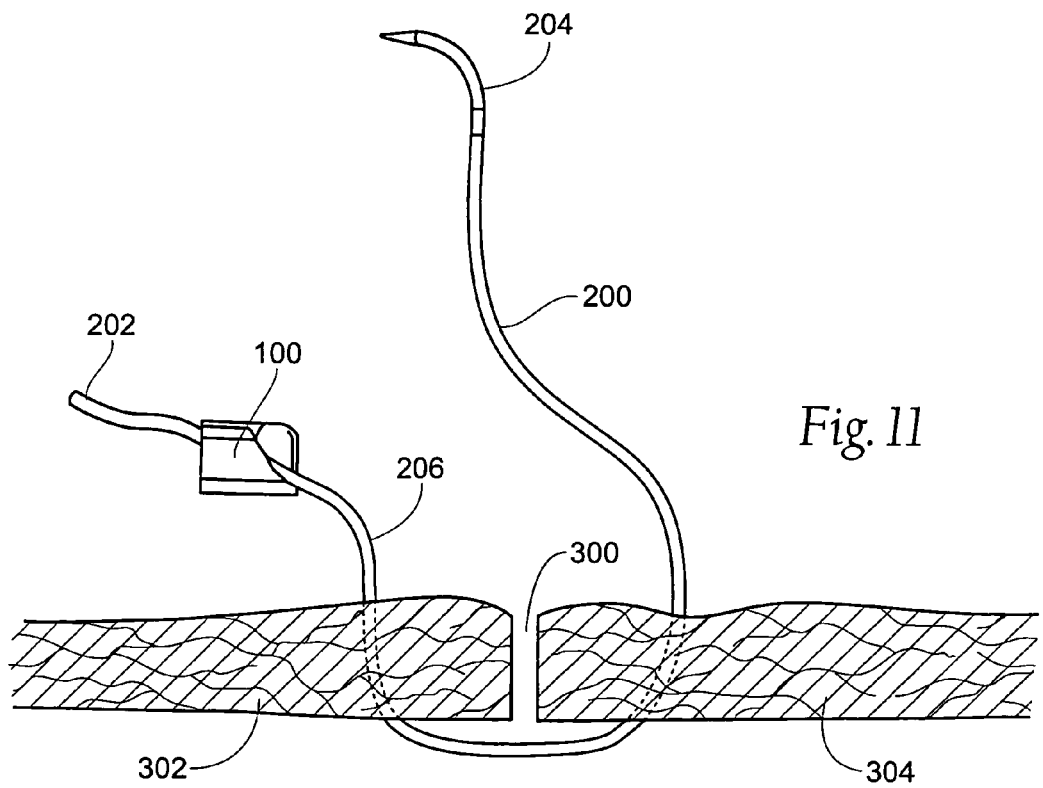
FIG. 11 is a front elevation view of the embodiment of FIG. 10 with the suture thread advanced through two opposing portions of tissue.

FIG. 11 depicts the embodiment of FIG. 10 having been partially inserted into two portions of tissue to close a suture 300. The needle 204 was inserted down through a desired amount of a first tissue portion 302 on one side of the suture 300 and up through a desired amount of a second tissue portion 304 on the opposite side of the suture 300. The thread 200 may have been advanced in this manner by the use of either a physician's hand directly or a needle driver (not shown) by way of a physician's hand guiding the needle 204. This guiding can be through both portions 302,304 of the tissue with one motion or with two separate motions; one first through the first portion 302 followed by a second motion through the second portion 304. The portion of the thread between the suture lock 100 and the first tissue portion 302 forms a guide thread 206.

Figure 12:
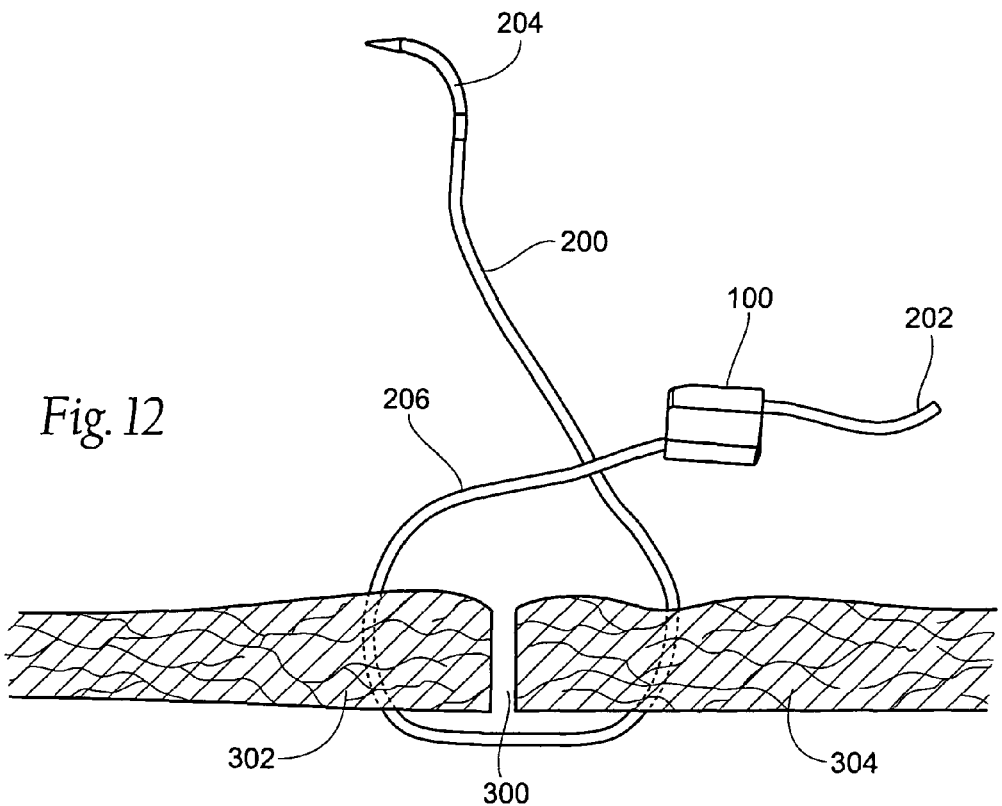
FIG. 12 is a first rear elevation view of the embodiment of FIG. 11 rotated about the free end of the suture thread.
Figure 13:
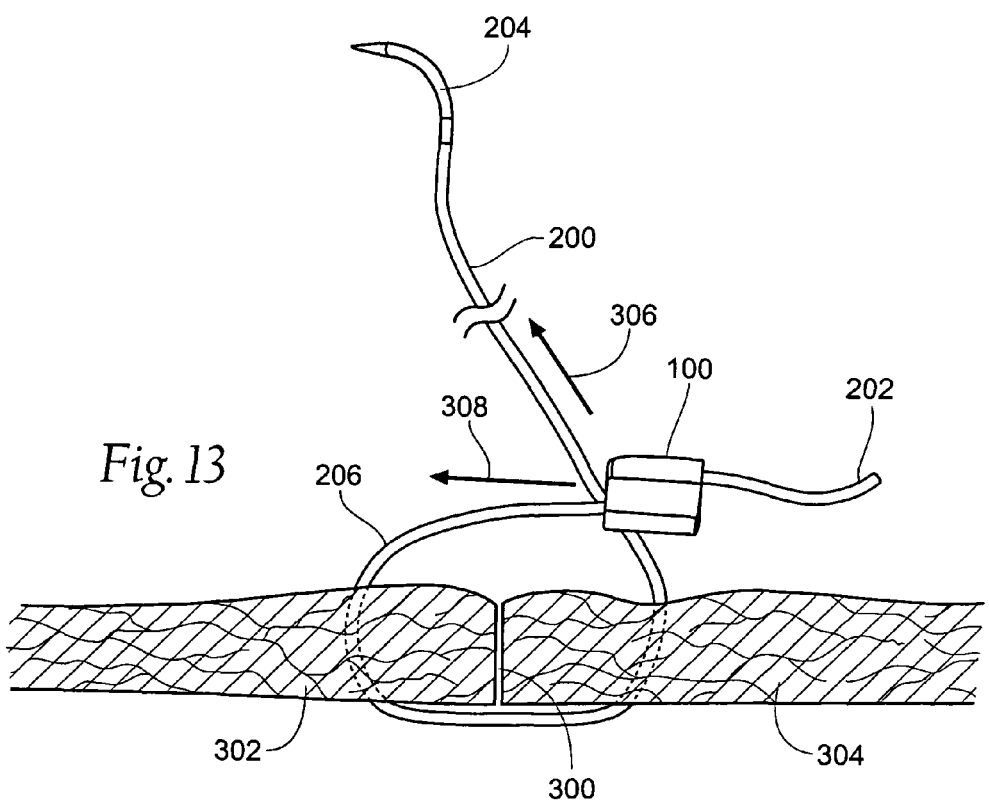
FIG. 13 is a second rear elevation view of the embodiment of FIG. 11 rotated about the free end of the suture thread, the suture thread free end advanced through the tissue such that it starts to engage the suture lock.

Next, the lock 100 is brought forward and turned in front of the free end of the suture thread 200 as seen in FIG. 12. This maneuver may be accomplished by a physician's hand, directly, or a needle driver or grasper grasping the working end 202 of the thread 200. Turning to FIG. 13, as the suture needle 204 and thread 200 are pulled in a first direction 306, the lock 100 will have a tendency towards a second direction 308. The free end of the suture thread 200 is preferably maintained in close proximity, or even touching or crossing, the guide thread 206, thereby guiding the suture thread 200 into the suture lock 100, thus securing the thread 200 to the lock 100 by the locking portion 120. Therefore, the suture thread 200 is preferably manipulated to the correct position by a combination of the guiding portion 160 of the lock 100, including the right guide wings 162,164, the top guide wings 168, 172, and the guide thread 206 acting as a guide rail. In this manner, the right guide wings 162,164 can compensate for variations in angular rotation between the first open end 126 of the first channel 124 and the plane of the free end of the suture thread 200. In effect, the tapered nature of the guide wings will rotate the first open end 126 to line up with the free end of the suture thread 200.

Figure 14:
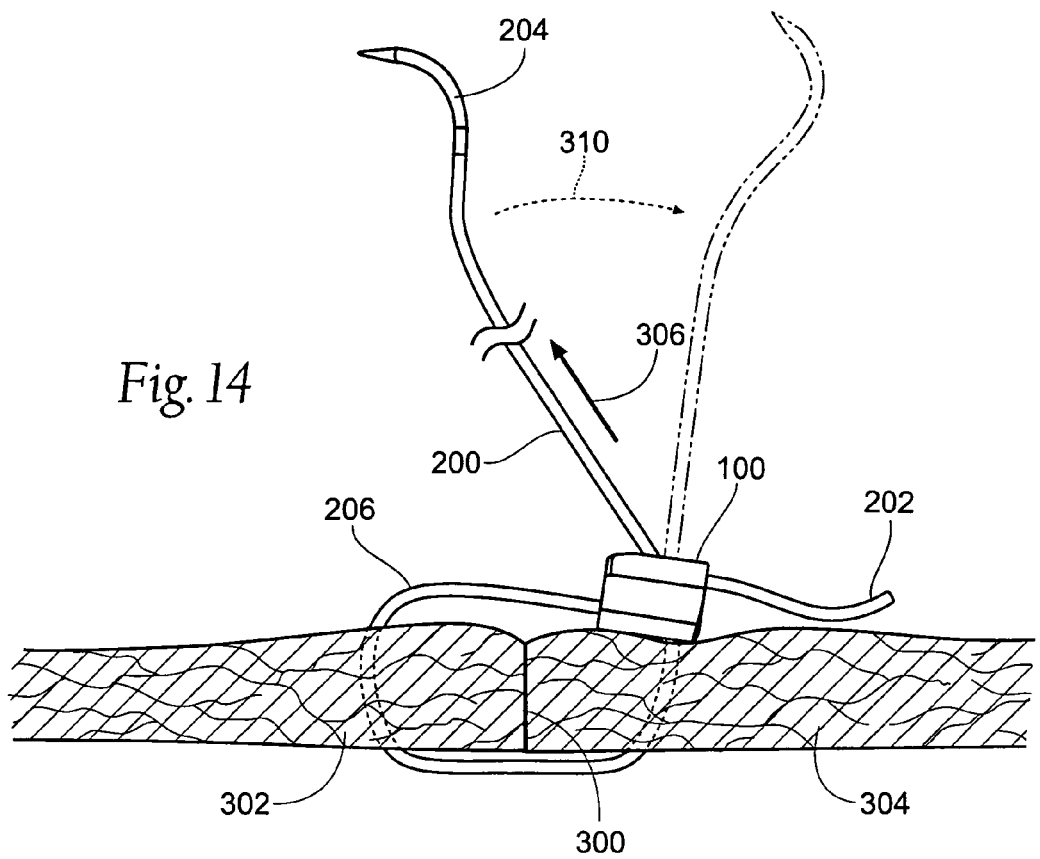
FIG. 14 is a third rear elevation view of the embodiment of FIG. 11 rotated about the free end of the suture thread, the suture thread free end further further advanced and further engaging the suture lock.
Figure 15:
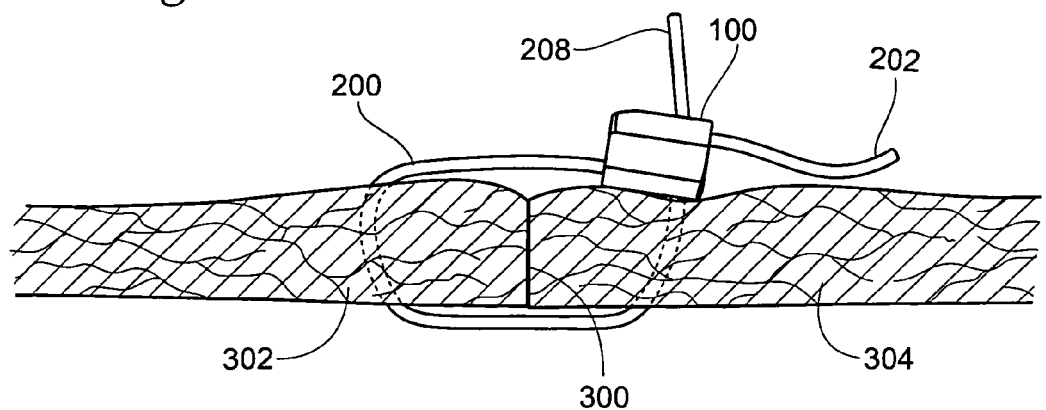
FIG. 15 is a fourth rear elevation view of the embodiment of FIG. 11 rotated about the free end of the suture thread, the suture thread free end fully engaging the suture lock having the free end trimmed.

The thread 200 is also tensioned to achieve desired approximation of the tissue portions 302,304 as seen in FIG. 14. This may be done by pulling the thread 200 in the first direction 306, and thereafter or simultaneously, if desired, in a third direction 310. If desired, the free end of the suture thread 200 can be pulled generally opposite the third direction 310 while the working end 202 or suture lock itself 100 is pulled generally in the third direction 310. This will release the tension on the suture 300 and the process can be repeated until the desired suture 300 tension is achieved. Finally, as shown in FIG. 15, the suture thread 200 may be trimmed, thereby leaving an adjustment thread 208, in the event that future adjustment of the suture 300 is required or desired.

Figure 16A:
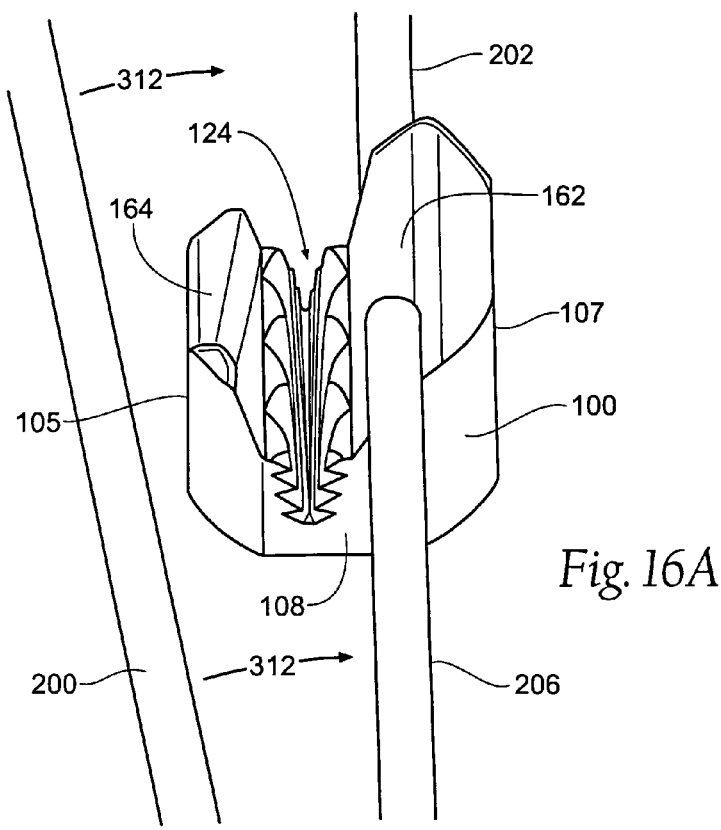
FIG. 16A is a first right bottom perspective view of the embodiment of FIG. 12 showing the suture thread free end moving in a first direction.
Figure 16B:
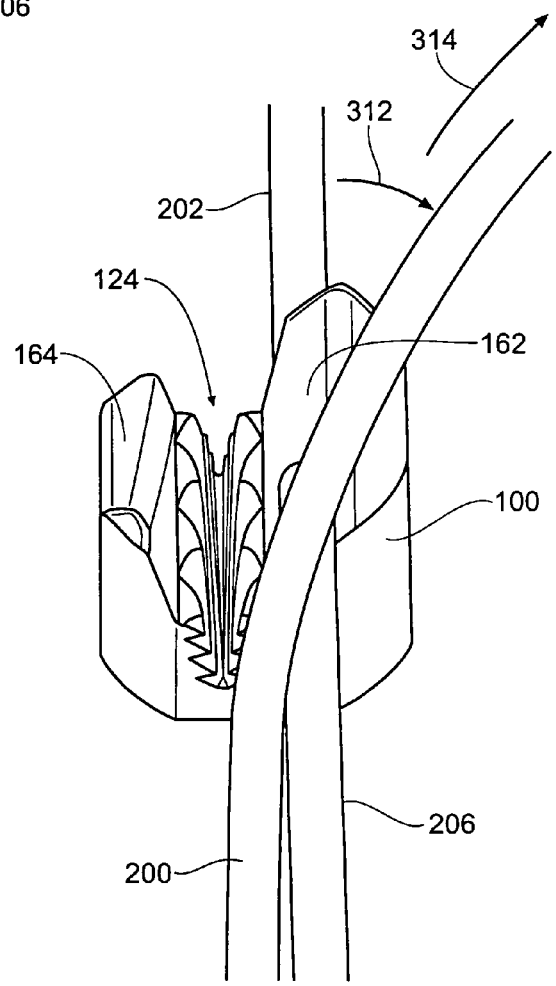
FIG. 16B is a second right bottom perspective view of the embodiment of FIG. 16A showing the suture thread free end engaging the suture guide thread.
Figure 16C:
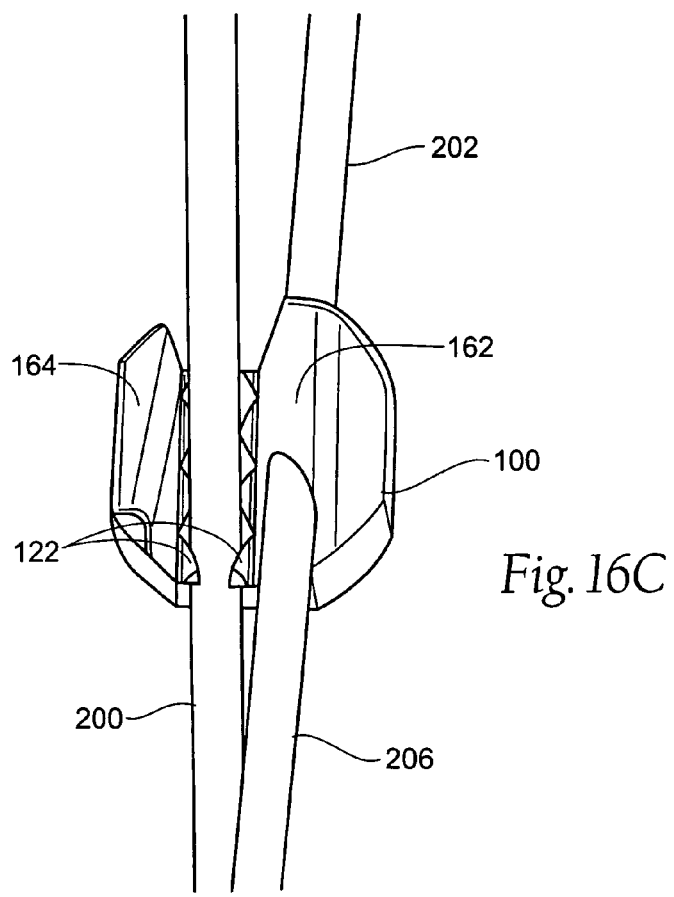
FIG. 16C is a third right bottom perspective view of the embodiment of FIG. 16A showing the suture thread free end engaged with the suture lock.

FIGS. 16A-16C depict a first method of engaging a suture thread with a locking portion of a suture lock using a device according to the present invention where a device has been provided, such as that shown in FIG. 10, including a suture thread 200 having a suture needle 204 coupled thereto, the suture thread 200 having been coupled to a suture lock 100. As described in connection with FIGS. 11-12, the needle 204 has been inserted through tissue portions and it is now desirable to engage the suture thread 200 with the lock 100. The portion of the thread 200 between the suture lock 100 and the first tissue portion 302 forms a guide thread 206. The thread 200 is maneuvered in a direction 312, generally laterally towards the front surface 105 and the bottom surface 108, and is brought into contact with the guide thread 206, as shown in FIG. 16B, and then, or contemporaneously, pulled taught in another direction 314. The thread 200 may, as shown in FIG. 16C, then be slid along the guide thread 206, into the first channel 124 to engage teeth 122 disposed in the channel 124.

Figure 17A:
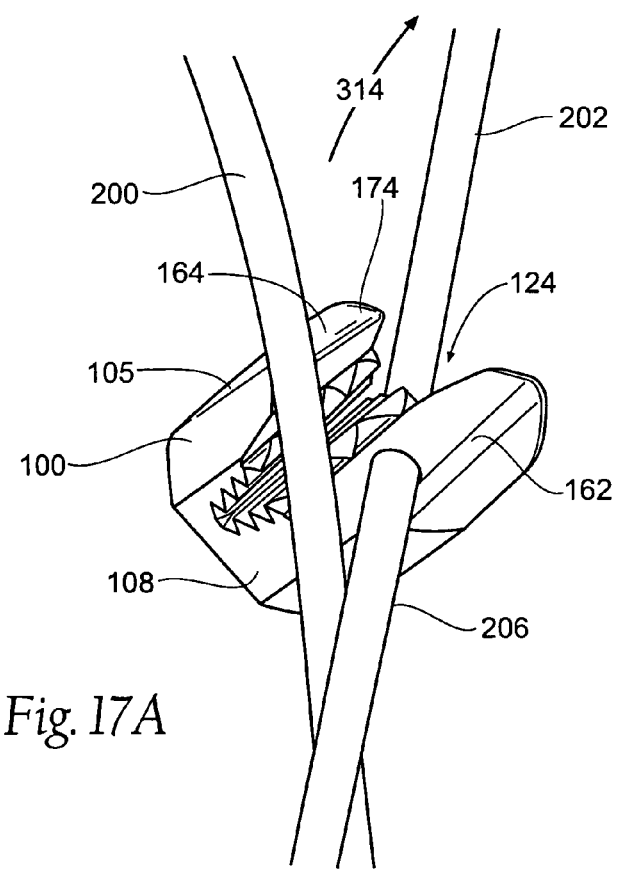
FIG. 17A is a first right bottom perspective view of the embodiment of FIG. 12 showing a suture thread engaging a guide thread and a suture lock from a second direction.
Figure 17B:
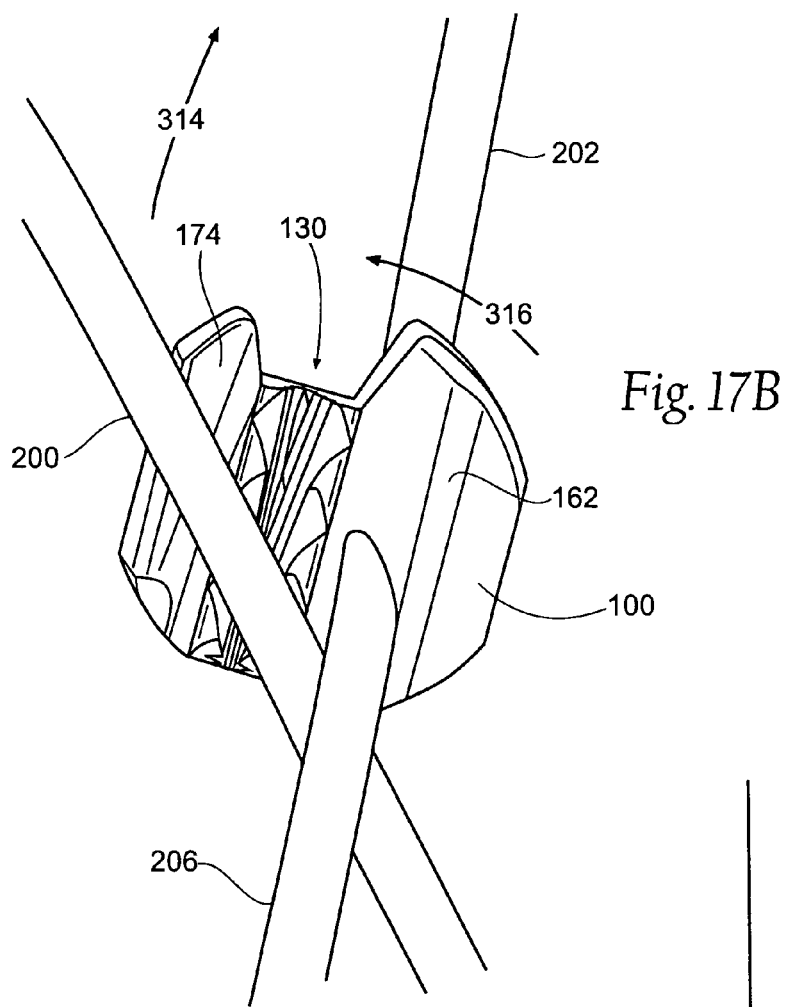
FIG. 17B is a right front perspective view of the embodiment of FIG. 17A showing the suture thread engaging the front right guide wing and the guide thread.
Figure 17C:
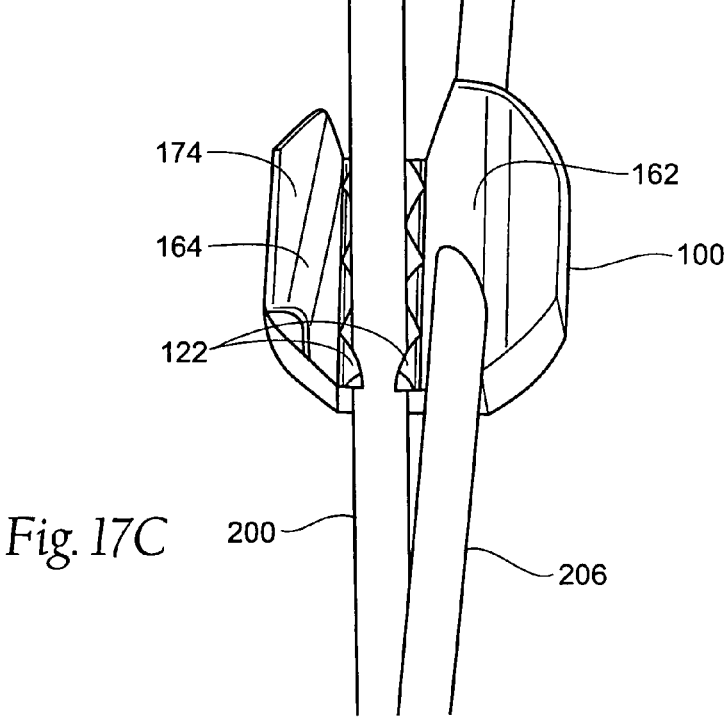
FIG. 17C is a second right bottom perspective view of the embodiment of FIG. 17A showing the suture thread engaged with the suture lock.

FIGS. 17A-17C depict a second method of engaging a suture thread with a locking portion of a suture lock using a device according to the present invention where a device has been provided, such as that shown in FIG. 10, including a suture thread 200 having a suture needle 204 coupled thereto, the suture thread 200 having been coupled to a suture lock 100. As described in connection with FIGS. 11-12, the needle 204 has been inserted through tissue portions and it is now desirable to engage the suture thread 200 with the lock 100. The portion of the thread 200 between the suture lock 100 and the first tissue portion 302 forms a guide thread 206. The thread 200 is maneuvered in a direction 314, generally laterally towards the bottom surface 108, and is brought into contact with the guide thread 206, and the insertion chamfer 174 of the front right guide wing 164. The contact of the thread 200 with the guide thread 206 and the insertion chamfer 174 causes the lock 100 to rotate 316, as shown in FIG. 17B. As the suture thread 200 is tightened, as shown in FIG. 17C, the thread 200 is situated in the first channel 124, thereby engaging the teeth 122 disposed therein.

Figure 18:
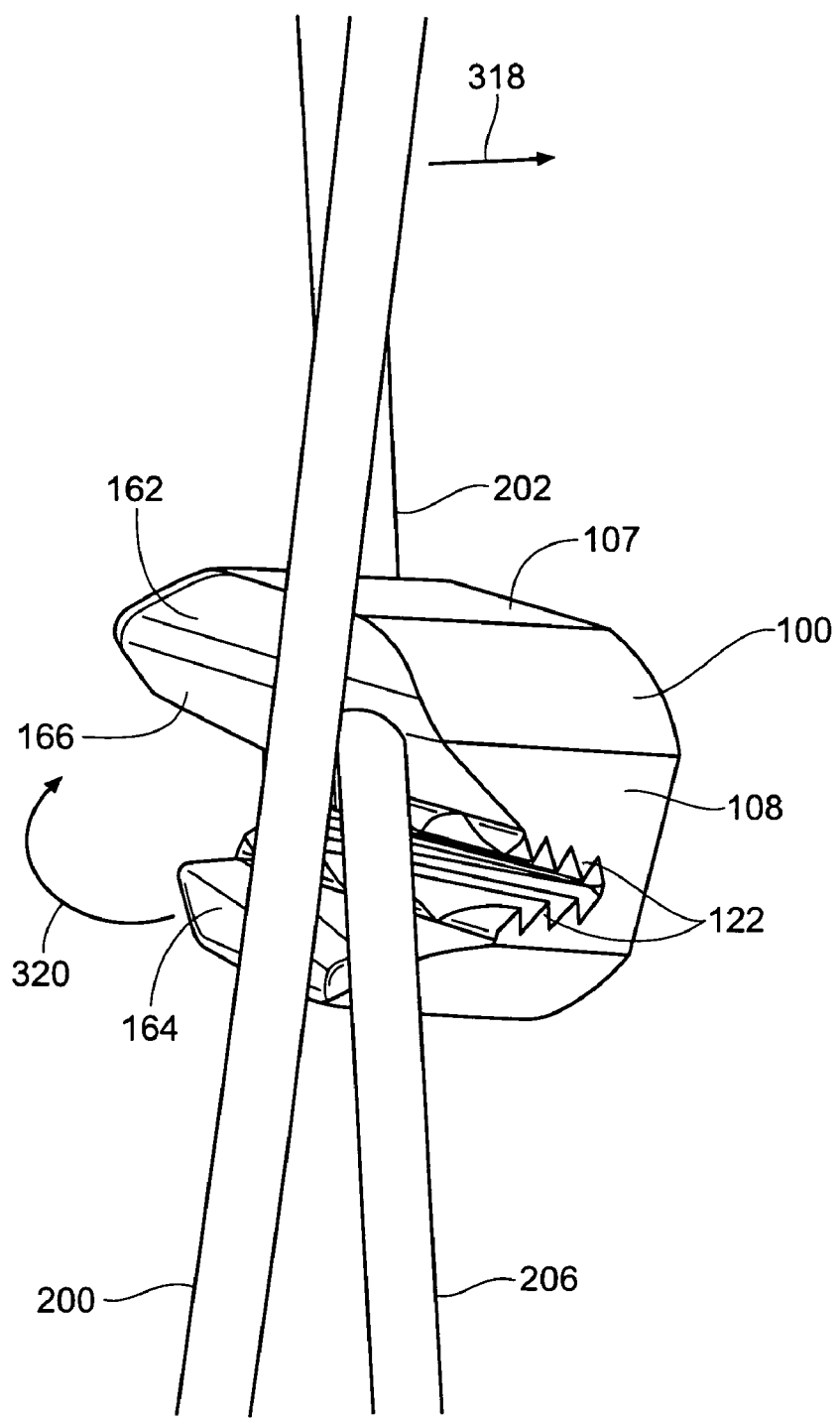
FIG. 18 is a right bottom perspective view of the embodiment of FIG. 12 showing a suture thread engaging a guide thread and a suture lock from a third direction.

FIG. 18 depicts a third method of engaging a suture thread with a locking portion of a suture lock using a device according to the present invention where a device has been provided, such as that shown in FIG. 10, including a suture thread 200 having a suture needle 204 coupled thereto, the suture thread 200 having been coupled to a suture lock 100. As described in connection with FIGS. 11-12, the needle 204 has been inserted through tissue portions and it is now desirable to engage the suture thread 200 with the lock 100. The portion of the thread 200 between the suture lock 100 and the first tissue portion 302 forms a guide thread 206. The thread 200 is maneuvered in a direction 318, generally laterally towards the right surface 104, slightly below the bottom surface 108, and is brought into contact with the guide thread 206 and the back right guide wing 162. The contact of the thread 200 with the rounded right surface of the back right guide wing 162 causes the lock 100 to S rotate 320. As the suture thread 200 is tightened, the thread 200 is situated in the first channel 124, thereby engaging the teeth 122 disposed therein.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A suture lock comprising:
  a suture lock body having
    a front surface generally opposed from a back surface,
    a left surface extending at least partially between and coupled to said front surface and said back surface,
    a right surface generally opposed from said left surface, said right surface and said left surface defining a width therebetween,
    a bottom surface extending between and coupled to said front surface and said back surface, and extending between and coupled to said right surface and said left surface, and
    a top surface generally opposed from said bottom surface, said top surface and said bottom surface defining a height therebetween;

a first channel formed in said right surface, said first channel extending longitudinally through said top surface and through said bottom surface, said first channel extending laterally between said front surface and said back surface, said first channel extending between a first open end at said right surface and a first terminal end, and said first channel defining generally opposed front and back right guide wings;

a suture locking mechanism disposed in said first channel comprising a plurality of teeth, at least two of said plurality of teeth having converging longitudinal edges; and a suture attachment site separated from said suture locking mechanism, said suture attachment site comprising a through bore extending through said left surface and through said back right guide wing.

2. A suture lock according to claim 1, said plurality of teeth comprising at least one pair of symmetrical teeth.

3. A suture lock according to claim 2, said plurality of teeth comprising a plurality of pairs of symmetrical teeth.

4. A suture lock according to claim 1, said converging longitudinal edges being at least substantially coplanar.

5. A suture lock according to claim 1, said through bore being formed along a longitudinal bore axis, said longitudinal bore axis disposed at a through bore angle relative to said bottom surface.

6. A suture lock according to claim 5, said longitudinal bore axis being oriented substantially perpendicular skew to said converging longitudinal edges of said at least two teeth.

7. A suture lock according to claim 5, said through bore angle comprising an angle of between about zero degrees and about forty-five degrees.

8. A suture lock according to claim 7, said through bore angle comprising an angle of about twenty-five degrees.

9. A suture lock according to claim 8, said suture lock further comprising a suture thread extending at least partially through said through bore, said suture thread being affixed to said suture lock body.

10. A suture lock according to claim 9, said suture thread being affixed to said suture lock body by adhesive.

11. A suture lock according to claim 1, said front right guide wing and said back right guide wing being asymmetric.

12. A suture lock according to claim 11, said front right guide wing comprising a sloped top surface.

13. A suture lock according to claim 1, said first open end being laterally wider than said first terminal end.

14. A suture lock according to claim 1, said suture lock comprising a material that naturally dissolves within a human body.

15. A suture lock according to claim 1, said suture lock body comprising a unitary body.

16. The suture lock according to claim 1, at least two of said teeth located closer to said first terminal end than said first open end.

17. The suture lock according to claim 16, at least two pairs of said teeth located closer to said first terminal end than to said first open end.

18. A suture lock according to claim 1, said locking mechanism comprising a predetermined grit of abrasive bonded to at least a portion of said first channel.

19. A suture lock comprising:

a suture lock body having:

a front surface generally opposed from a back surface, a left surface extending at least partially between and coupled to said front surface and said back surface, a right surface generally opposed from said left surface, said right surface and said left surface defining a width therebetween, a bottom surface extending between and coupled to said front surface and said back surface, and extending between and coupled to said right surface and said left surface, and a top surface generally opposed from said bottom surface, said top surface and said bottom surface defining a height therebetween;

a first channel formed in said right surface, said first channel extending longitudinally through said top surface and through said bottom surface, said first channel extending laterally between said front surface and said back surface, said first channel extending between a first open end at said right surface and a first terminal end, and said first channel defining generally opposed front and back right guide wings;

a second channel formed in said top surface, said second channel extending longitudinally through said left surface and through said terminal end of said first channel, said second channel extending laterally between said front surface and said back surface, said second channel extending between a second open end at said top surface and a second terminal end, and said second channel forming generally opposed front and back top guide wings;

a suture locking mechanism disposed in said first channel; and a suture attachment site separated from said suture locking mechanism.

20. A suture lock according to claim 19, said first open end being laterally wider than said first terminal end, and said second open end being laterally wider than said second terminal end.

21. A suture lock according to claim 19, said height measured through said front top guide wing being less than said height measured through said back top guide wing.

* * * * *